United States Patent [19]

Takada et al.

[11] Patent Number: 5,716,554
[45] Date of Patent: Feb. 10, 1998

[54] ULTRAVIOLET LIGHT ABSORBENT

[75] Inventors: Sadaki Takada; Toshihiko Nakane, both of Yokohama; Tsuyoshi Tsuchiya, Tokyo; Yutaka Nishida, Inagi, all of Japan

[73] Assignees: Shiseido Co., Ltd.; The Nisshin Oil Mills, Ltd., both of Tokyo, Japan

[21] Appl. No.: 603,258

[22] Filed: Feb. 20, 1996

[30] Foreign Application Priority Data

Feb. 21, 1995 [JP] Japan ............ 7-056500
Feb. 21, 1995 [JP] Japan ............ 7-056501

[51] Int. Cl.$^6$ ............ F21V 9/04
[52] U.S. Cl. ............ 252/589; 424/59; 424/60
[58] Field of Search ............ 252/589; 424/59, 424/60

[56] References Cited

U.S. PATENT DOCUMENTS

| | | | |
|---|---|---|---|
| 4,322,544 | 3/1982 | Okazaki et al. | 424/60 |
| 4,804,531 | 2/1989 | Grollier | 424/59 |
| 4,833,259 | 5/1989 | Erlemann et al. | 424/60 |
| 5,318,774 | 6/1994 | Alban et al. | 424/59 |
| 5,573,754 | 11/1996 | Kulkarni et al. | 424/59 |

FOREIGN PATENT DOCUMENTS

| | | |
|---|---|---|
| 2453132 | 10/1980 | France . |
| 2283173 | 5/1995 | United Kingdom . |
| WOA9407460 | 4/1994 | WIPO . |

*Primary Examiner*—Philip Tucker
*Attorney, Agent, or Firm*—Townsend & Banta

[57] ABSTRACT

An ultraviolet light absorbent comprising an ester mixture derived from esterification of pentaerythritol or trimethylolpropane and a saturated branched-chain fatty acid with a carbon number of 8-18 and ortho- or paramethoxycinnamic acid in a specific ratio. The ultraviolet light absorbent with prescribed ultraviolet light absorbing power has a moderate viscosity and can be handled and worked without inconvenience and/or difficulty.

6 Claims, No Drawings

ULTRAVIOLET LIGHT ABSORBENT

FIELD OF THE INVENTION

The present invention relates to an ultraviolet light absorbent comprising a mixture of ester compounds with specific compositions derived from pentaerythritol or trimethylolpropane, saturated branched-chain fatty acid with a carbon number of 8-18 and methoxycinnamic acid.

BACKGROUND OF THE INVENTION

The ultraviolet light which reaches the earth, although it is only approximately 6% of the sunlight, causes coloration, decoloration, reduced strength, destruction, etc. of rubber, paints, ink, etc., leading to degradation of their quality. In order to prevent such degradation due to the ultraviolet light, an ultraviolet light absorbent(s) is added to products which contain these products and materials.

Also, the ultraviolet light causes acute skin reactions such as erythema and darkening and, in the long term, causes skin aging and/or cancer. Due to this, sunscreening cosmetics containing ultraviolet light absorbents and/or ultraviolet light scattering agents to address misgivings about the ill effect of the ultraviolet light on the skin have been widely developed and various such products have been introduced to the market.

The ultraviolet light absorbents added to these products are structurally classified into the cinnamic acid type, PABA type, benzophenone type, salicylic acid type, heterocyclic type, camphor type, dibenzoylmethane type, chalcone type, etc., and many ultraviolet light absorbents have been developed. However, selection of the ultraviolet light absorbents used on human skin is limited due to safety, the feel of use on the skin, as well as solubility when blended into sunscreens. Therefore, among many ultraviolet light absorbents developed thus far, the cinnamic acid type and benzophenone type ultraviolet light absorbents have been used more frequently for endermic liniments.

When designing a paramethoxycinnamic acid ester compound for an ultraviolet light absorbent which can be used in cosmetics, the following points have to be considered. That is, esters formed from paramethoxycinnamic acid and low molecular weight lower alcohols may irritate skin. On the other hind, esters formed from high molecular weight alcohols, although they are an improvement in terms of skin irritation, have reduced ultraviolet light absorbing ability, a tendency to increase the melting point of the ester, poor compatibility with other ingredients, and high consistency even if they are liquid, leading to reduced workability when manufacturing cosmetics.

Esters formed from paramethoxycinnamic acid and ethylene glycol, glycerol, etc. are also known as ultraviolet light absorbents. However, similar to said esters formed from said higher alcohols, they are highly viscous or solid at room temperature, and therefore there is a problem in that compatibility with other raw materials is poor, leading to a limited range of application.

In addition, cosmetics containing paramethoxycinnamic acid esters, due to the high melting points and low compatibility of said esters, demand a high level of skill when designing the recipe of the product. Even with highly skilled designing, there is a problem in that crystal deposition, precipitation, demulsification, etc. are induced as time goes on, resulting in a reduction in ultraviolet light absorbing power and a degradation in quality, such as oxidation, polymerization and deterioration (coloring, offensive taste, offensive odor and putrefaction). Engineering countermeasures for this problem has been a significant challenge.

The inventors conducted earnest research to address the aforementioned problem and discovered that an ester mixture of pentaerythritol with a specific composition containing methoxycinnamic acid ester solved the aforementioned problem, thus completing the present invention.

SUMMARY OF THE INVENTION

An object of the present invention, for the purpose of fundamentally solving the aforementioned problem when using methoxycinnamic acid esters with ultraviolet light absorbing power in cosmetics, is to provide an ultraviolet light absorbent which is highly safe and maintains the prescribed ultraviolet light absorbing power while having excellent compatibility with other ingredients and causing no quality degradation.

More specifically, the present invention is an ultraviolet light absorbent comprising either mixtures of esters represented by the following formulas (I), (II) and (III) or mixtures of esters represented by formulas (IV), (V) and (VI):

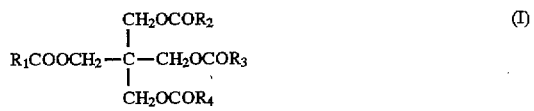

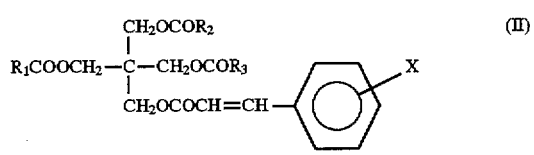

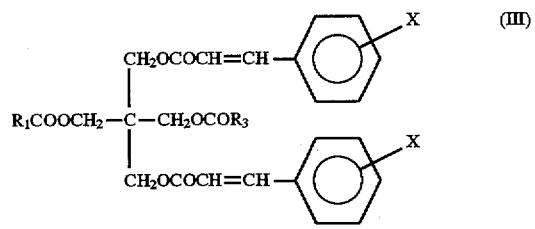

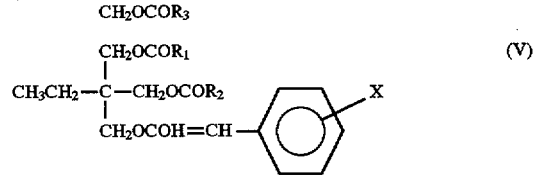

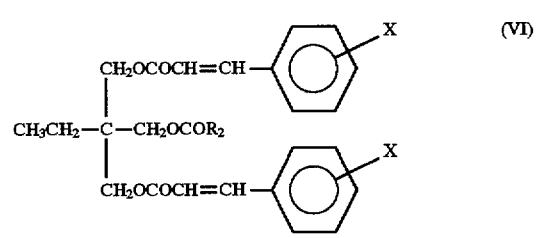

wherein $R_1$, $R_2$, $R_3$ and $R_4$, which can be identical to or different from each other, denote alkyl groups derived from a saturated branched-chain fatty acid with a carbon number of 7-17, and X denotes a methoxyl group with an ortho and/or para position.

The present invention is also an ultraviolet light absorbent comprising mixtures of esters represented by formulas (I), (II) and (III) or mixtures of esters represented by formulas (IV), (V) and (VI), wherein the composition ratio (weight ratio) of the esters represented by the formulas (I), (II) and (III) is (I):(II):(III)=58–65:30–35:3–7 and the maximum absorbance of 0.1–0.5 occurs at the peak absorption wavelength of 312 nm when the ultraviolet light absorption spectrum is measured using a 10 ppm ethanol solution.

Further, the present invention is also an ultraviolet light absorbent comprising an ester mixture represented by formulas (I), (II) and (III) or mixtures of esters represented by formulas (IV), (V) and (VI), wherein $R_1$, $R_2$, $R_3$ and $R_4$ are all identical and are residues derived from 2-ethylhexanoic acid by removing the carboxyl group, and X denotes a methoxyl group with a para position.

In addition, the present invention is also an ultraviolet light absorbent comprising a mixture of ester compounds obtained by esterification using 3.0–3.8 moles of 2-ethylhexanoic acid and 0.2–1.0 moles of paramethoxycinnamic acid for 1 mole of pentaerythritol.

Also, the present invention is also an ultraviolet light absorbent comprising a mixture of ester compounds obtained by esterification using 2.0–2.8 moles of 2-ethylhexanoic acid and 0.2–1.0 moles of paramethoxycinnamic acid for 1 mole of trimethylolpropane.

The present invention is described in detail below.

DETAILED DESCRIPTION OF THE INVENTION

The ultraviolet light absorbent of the present invention comprises an ester mixture derived from esterification of pentaerythritol or trimethylolpropane and a saturated branched-chain fatty acid with a carbon number of 8-18 and ortho- or paramethoxycinnamic acid in a specific ratio.

In one embodiment, it comprises tetraester (Formula (I)) which is 4 moles of a saturated branched-chain fatty acid with a carbon number of 8-18 esterified with 1 mole of pentaerythritol, tetraester (Formula (II)) which is 3 moles of a saturated branched-chain fatty acid with a carbon number of 8-18 and 1 mole of ortho- or paramethoxycinnamic acid esterified with 1 mole of pentaerythritol and tetraester (Formula (III) which is 2 moles of a saturated branched-chain fatty acid with a carbon number of 8-18 and 2 moles of ortho- or paramethoxycinnamic acid esterified with 1 mole of pentaerythritol.

In another embodiment, it comprises triester (Formula (IV)) which is 3 moles of a saturated branched-chain fatty acid with a carbon number of 8-18 esterified with 1 mole of trimethylolpropane, triester (Formula (V)) which is 2 moles of a saturated branched-chain fatty acid with a carbon number of 8-18 and 1 mole of ortho- or paramethoxycinnamic acid esterified with 1 mole of trimethylolpropane and triester (Formula (VI)) which is 1 mole of a saturated branched-chain fatty acid with a carbon number of 8-18 and 2 moles of ortho- or paramethoxycinnamic acid esterified with 1 mole of trimethylolpropane.

For the saturated branched-chain fatty acid with a carbon number of 8-18 to be esterified, a single type of saturated branched-chain fatty acid can be used, but multiple types of saturated branched-chain fatty acids can also be used.

Specific examples include isooctylic acid (2-ethylhexanoic acid, 2,4,4-trimethylpentanoic acid), isononanic acid (3,5,5-trimethylhexanoic acid), isodecanoic acid (3,7-dimethyloctanoic acid), isododecanoic acid (6-propylnonanic acid), neotridecanoic acid, isotetradecanoic acid (12-methyltridecanoic acid), isopentadecanoic acid (2-methyltetradecanoic acid, 5-methyltetradecanoic acid), isohexadecanoic acid (2,2-dimethyltetradecanoic acid), isostearic acid (2-heptylundecanoic acid) and isostearic acid from Emery Co., Ltd. which has multi-methyl branched chains.

Among the aforementioned saturated branched-chain fatty acids, the most preferable is to use 2-ethylhexanoic acid alone.

For the methoxycinnamic acid, those with a methoxyl group at the ortho and/or para position can be used. More preferable is paramethoxycinnamic acid.

The aforementioned tetraesters and triesters constituting the ultraviolet light absorbent of the present invention can be prepared using a prior art method. The method can be chosen from among the direct ester synthesis method, the transesterification method, the method in which individual esters are mixed, etc.

In the direct ester synthesis method, prescribed amounts (reaction equivalents) of trimethylolpropane or pentaerythritol, one or more types of saturated branched-chain fatty acids with a carbon number of 8-18 and ortho- or paramethoxycinnamic acid are mixed and the reaction is carried out without catalysts or in the presence of an esterification catalyst(s) such as sulfuric acid, hydrochloric acid, phosphoric acid, paratoluenesulfonic acid as well as nickel, tin, titanium and oxides and chlorides of these metals, without solvents or with a nonaqueous solvent(s) such as xylene and toluene. Purification treatments such as alkali deoxidation, decoloring using activated carbon, silica-gel fractionation, and vacuum deodorization are given to the esterified reactant to obtain the ultraviolet light absorbent comprising the ester mixture of the present invention.

For example, 3.0–3.8 moles of 2-ethylhexanoic acid and 0.2–1.0 moles of paramethoxycinnamic acid for 1 mole of pentaerythritol can be used for esterification with the direct ester synthesis method to obtain the ultraviolet light absorbent of the present invention.

As another example, 2.0–2.8 moles of 2-ethylhexanoic acid and 0.2–1.0 moles of paramethoxycinnamic acid for 1 mole of trimethylolpropane can be used for esterification with the direct ester synthesis method to obtain the ultraviolet light absorbent of the present invention.

In the transesterification method, a metal alkolate(s) such as sodium methoxide and potassium methoxide or an alkaline substance(s) such as sodium hydroxide, potassium hydroxide and sodium carbonate is used as the catalyst. Reaction equivalents of pentaerythritol or trimethylolpropane, one or more types of lower alcohol (carbon number: 1-4) esters of a saturated branched-chain fatty acid with a carbon number of 8-18 and lower alcohol (carbon number: 1-4) esters of ortho- or paramethoxycinnamic acid are mixed, and the transesterification reaction is carried out in a virtually anhydrous condition at 50°–200° C., more preferably 100°–180° C., for 20–40 hours, followed by the same purification treatments as for said direct ester synthesis method.

The ultraviolet light absorbent of the present invention can also be prepared by preparing individual esters represented by Formulas (I), (II), (III), (IV), (V) and (VI), by means of said ester synthesis method or transesterification method and then mixing the desired amounts of them together.

The ultraviolet light absorbent of the present invention can contain the tetraesters represented by the Formulas (I), (II) and (III), and the triesters represented by Formulas (IV), (V) and (VI), in any mixing ratio. However, the weight ratio is preferably (I):(II):(III)=58–65:30–35:3–7, and more preferably (I):(II):(III)=60–63:32–33:4–5; or the weight ratio is preferably (IV):(V):(VI)=58–65:30–35:3–7, and more preferably (IV):(V):(VI)=60–63:32–33:4–5. Also, those whose maximum absorbance of 0.1–0.5 occurs at a peak absorption wavelength (λ max) of 312 nm when the ultraviolet light absorption spectrum is measured using a 10 ppm ethanol solution are more preferable, and the most preferable are those whose maximum absorbance of 0.15–0.3 occurs at this peak absorption wavelength.

If the amount of the tetraester or triester containing methoxycinnamic acid residue is more than the aforementioned range, then the viscosity sharply increases and workability when using the ultraviolet light absorbent becomes poor, and compatibility with other ingredients will also be reduced. On the other hand, if the amount of the tetraester or triester containing methoxycinnamic acid residue is more than the aforementioned range, then the ultraviolet light absorbing power per unit amount used decreases and it becomes harder to obtain desired effects.

A desirable embodiment of the ultraviolet light absorbent of the present invention is a mixture of (I) pentaerythritol tetra 2-ethylhexanoic acid ester, (II) pentaerythritol tri 2-ethylhexanoic acid monoparamethoxycinnamic acid ester and (III) pentaerythritol di 2-ethylhexanoic acid diparamethoxycinnamic acid ester with a composition ratio (weight ratio) of 60–63:32–33:4–5 wherein the mixture (I)+(II)+(III) is prepared such that the maximum absorbance is 0.15–0.3 when the ultraviolet light absorption spectrum is measured using a 10 ppm ethanol solution.

Another desirable embodiment of the ultraviolet light absorbent of the present invention is a mixture of (IV) trimethylolpropane tri 2-ethylhexanoic acid ester, (V) trimethylolpropane di 2-ethylhexanoic acid monoparamethoxycinnamic acid ester and (VI) trimethylolpropane mono 2-ethylhexanoic acid diparamethoxycinnamic acid ester with a composition ratio (weight ratio) of 60–63:32–33:4–5 wherein the mixture (IV)+(V)+(VI) is prepared such that the maximum absorbance is 0.15–0.3 when the ultraviolet light absorption spectrum is measured using a 10 ppm ethanol solution.

Applications of the ultraviolet light absorbent of the present invention are not limited, and it can be blended in conventional cosmetics which contain ultraviolet light absorbents such as sunscreen creams, sunscreen lotions, lipsticks, sunscreen oils and sunscreen gels.

In so doing, part or all of the conventional ultraviolet light absorbent can be replaced with the ultraviolet light absorbent of the present invention. The esters represented by the Formulas (I) and (IV), which are ingredients in the ultraviolet light absorbent of the present invention, are also useful as alternative oil agents for conventional oil bases. The amount of the ultraviolet light absorbent of the present invention added to cosmetics can be adjusted according to the type of the target cosmetic. In general, 5–50% of the total recipe, preferably 7–10%, should be used.

EXAMPLES

The present invention is described in detail below by referring to examples. The present invention is not limited to these examples.

Example 1

111.9 g of pentaerythritol, 73.2 g of paramethoxycinnamic acid and 414.9 g of 2-ethylhexanoic acid were put into a 1-liter 4-mouth flask equipped with a stirrer, a thermometer, a nitrogen gas blowing tube and a water separation tube. For the catalyst, tin chloride was added such that its amount would be 0.5 wt % of the whole mixture. For the refluxing solvent, xylene was added such that its amount would be 5 wt % of the whole mixture. The esterification reaction was carried out at 160°–240° C. for 30 hours, and the end of the reaction was detected as the point in time when the acid value of the reactant did not decrease any further. The mixture was then cooled down to room temperature, the catalyst was filtered out, the decoloring treatment was conducted using activated carbon and the deodorization treatment was conducted by blowing in water vapor at a 3 mmHg vacuum to obtain 395 g of a light yellow oily substance (sample A).

This substance had an acid value of 0.1, a hydroxyl value of 0.3, a degree of saponification of 345, a viscosity of 302 (centipoise/25° C.), and the maximum absorbance was 0.17 at λ max of 312 nm when the ultraviolet light absorption spectrum was measured using a 10 ppm ethanol solution.

Gas chromatography analysis indicated that there were 3 types of ingredients, i.e. pentaerythritol tetra 2-ethylhexanoic acid ester (a), pentaerythritol tri 2-ethylhexanoic acid monoparamethoxycinnamic acid ester (b) and pentaerythritol di 2-ethylhexanoic diparamethoxycinnamic acid ester (c), wherein the composition ratio (weight ratio) was a:b:c=62.5:32.5:5.0.

Compatibility between sample A, which is an ultraviolet light absorbent of the present invention, and generally used raw materials for cosmetics was excellent, as shown later in Table 1.

Example 2

108.3 g of pentaerythritol, 70.8 g of paramethoxycinnamic acid and 420.9 g of mixed fatty acids comprising 2-ethylhexanoic acid and 3,5,5-trimethylhexanoic acid (molar ratio 1:1) were used in the esterification and purification treatments in the same manner as in Example 1 to obtain 385 g of a light yellow oily substance (sample B).

Sample B had an acid value of 0.1, a hydroxyl value of 0.3, a degree of saponification of 330, a viscosity of 300 (centipoise/25° C.), and the maximum absorbance was 0.16 at λ max of 312 nm when the ultraviolet light absorption spectrum was measured using a 10 ppm ethanol solution.

Gas chromatography analysis, conducted in the same manner as in Example 1, indicated that there were 6 types of ingredients, i.e. pentaerythritol di 2-ethylhexanoic acid di 3,5,5-trimethylhexanoic acid ester (a), pentaerythritol tri 2-ethylhexanoic acid mono 3,5,5-trimethylhexanoic acid ester (b), pentaerythritol mono 2-ethylhexanoic acid tri 3,5,5-trimethylhexanoic acid ester (c), pentaerythritol di 2-ethylhexanoic acid mono 3,5,5-trimethylhexanoic acid monoparamethoxycinnamic acid ester (d), pentaerythritol mono 2-ethylhexanoic acid di 3,5,5-trimethylhexanoic acid monoparamethoxycinnamic acid ester (e) and pentaerythritol mono 2-ethylhexanoic acid mono 3,5,5-trimethylhexanoic acid diparamethoxycinnamic acid ester (f), wherein the composition ratio (weight ratio) was (a+b+c):(d+e):f=62:33:5.

Compatibility between sample B and generally used raw materials for cosmetics was excellent, as shown later in Table 1.

Example 3

104.1 g of pentaerythritol, 108.9 g of paramethoxycinnamic acid and 387.0 g of 3,5,5-trimethylhexanoic acid were used in the esterification and purification treatments in the same manner as in Example 1 to obtain 392 g of a light yellow oily substance (sample C). Sample C had an acid value of 0.1, a hydroxyl value of 0.4, a degree of saponification of 318, a viscosity of 308 centipoise/25° C., and the maximum absorbance was 0.17 at λ max of 312 nm when the ultraviolet light absorption spectrum was measured in the same manner as in Example 1. Gas chromatography analysis indicated that there were 3 types of ingredients, i.e. pentaerythritol tetra 3,5,5-trimethylhexanoic acid ester (a), pentaerythritol tri 3,5,5-trimethylhexanoic acid monoparamethoxycinnamic acid ester (b) and pentaerythritol di 3,5,5-trimethylhexanoic acid diparamethoxycinnamic acid ester (c), wherein the composition ratio (weight ratio) was a:b:c=60.8:33.7:5.5. Compatibility between sample C and generally used raw materials for cosmetics was excellent, as shown later in Table 1.

Example 4

111.4 g of pentaerythritol, 87.5 g of orthomethoxycinnamic acid and 401.1 g of 2-ethylhexanoic acid were used in the esterification and purification treatments in the same manner as in Example 1 to obtain 390 g of a light yellow oily substance (sample D). Sample D had an acid value of 0.1, a hydroxyl value of 0.3, a degree of saponification of 342, a viscosity of 303 centipoise/25° C., and the maximum absorbance was 0.17 at λ max of 312 nm when the ultraviolet light absorption spectrum was measured in the same manner as in Example 1. Gas chromatography analysis indicated that there were 3 types of ingredients, i.e. pentaerythritol tetra 2-ethylhexanoic acid ester (a), pentaerythritol tri 2-ethylhexanoic acid monoorthomethoxycinnamic acid ester (b) and pentaerythritol di 2-ethylhexanoic acid diorthomethoxycinnamic acid ester (c), wherein the composition ratio (weight ratio) was a:b:c=63.0:32.5:4.5. Compatibility between sample D and generally used raw materials for cosmetics was excellent, as shown later in Table 1.

Example 5

66.9 g of pentaerythritol, 43.8 g of paramethoxycinnamic acid and 489.3 g of 2-heptylundecanoic acid were used in the esterification and purification treatments in the same manner as in Example 1 to obtain 394 g of a light yellow oily substance (sample E). Sample E had an acid value of 0.1, a hydroxyl value of 0.4, a degree of saponification of 194, a viscosity of 348 centipoise/25° C., and the maximum absorbance was 0.15 at λ max of 312 nm when the ultraviolet light absorption spectrum was measured in the same manner as in Example 1. Gas chromatography analysis indicated that there were 3 types of ingredients, i.e. pentaerythritol tetra 2-heptylundecanoic acid ester (a), pentaerythritol tri 2-heptylundecanoic acid monoparamethoxycinnamic acid ester (b) and pentaerythritol di 2-heptylundecanoic acid diparamethoxycinnamic acid ester (c), wherein the composition ratio (weight ratio) was a:b:c=64:32:4. Compatibility between sample E and generally used raw materials for cosmetics was excellent, as shown later in Table 1.

Example 6

137.9 g of trimethylolpropane, 91.6 g of paramethoxycinnamic acid and 370.5 g of 2-ethylhexanoic acid were put into a 1-liter 4-mouth flask equipped with a stirrer, a thermometer, a nitrogen gas blowing tube and a water separation tube. For the catalyst, tin chloride was added such that its amount would be 0.5 wt % of the whole mixture. For the refluxing solvent, xylene was added such that its amount would be 5 wt % of the whole mixture. The esterification reaction was carried out at 160°–240° C. for 30 hours, and the end of the reaction was detected as the point in time when the acid value of the reactant did not decrease any further. The mixture was then cooled down to room temperature, the catalyst was filtered out, the decoloring treatment was conducted using activated carbon and the deodorization treatment was conducted by blowing in water vapor at a 3 mmHg vacuum to obtain 390 g of a light yellow oily substance (sample H).

This substance had an acid value of 0.1, a hydroxyl value of 0.3, a degree of saponification of 319, a viscosity of 185 centipoise/25° C., and the maximum absorbance was 0.19 at λ max of 312 nm when the ultraviolet light absorption spectrum was measured using a 10 ppm ethanol solution.

Gas chromatography analysis indicated that there were 3 types of ingredients, i.e. trimethylolpropane tri 2-ethylhexanoic acid ester (a), trimethylolpropane di 2-ethylhexanoic acid monoparamethoxycinnamic acid ester (b) and trimethylolpropane mono 2-ethylhexanoic diparamethoxycinnamic acid ester (c), wherein the composition ratio (weight ratio) was a:b:c=62.5:33:4.5.

Compatibility between sample H, which is an ultraviolet light absorbent of the present invention, and generally used raw materials for cosmetics was excellent, as shown later in Table 2.

Example 7

133.9 g of trimethylolpropane, 88.9 g of paramethoxycinnamic acid and 377.2 g of mixed fatty acids comprising 2-ethylhexanoic acid and 3,5,5-trimethylhexanoic acid (molar ratio 1:1) were used in the esterification and purification treatments in the same manner as in Example 7 to obtain 395 g of a light yellow oily substance (sample I).

Sample I had an acid value of 0.1, a hydroxyl value of 0.4, a degree of saponification of 308, a viscosity of 199 centipoise/25° C., and the maximum absorbance was 0.18 at λ max of 312 nm when the ultraviolet light absorption spectrum was measured using a 10 ppm ethanol solution.

Gas chromatography analysis, conducted in the same manner as in Example 6, indicated that there were 7 types of ingredients, i.e. trimethylolpropane mono 2-ethylhexanoic acid di 3,5,5-trimethylhexanoic acid ester (a), trimethylolpropane di 2-ethylhexanoic acid mono 3,5,5-trimethylhexanoic acid ester (b), trimethylolpropane di 2-ethylhexanoic acid monoparamethoxycinnamic acid ester (c), trimethylolpropane di 3,5,5-trimethylhexanoic acid monoparamethoxycinnamic acid ester (d), trimethylolpropane mono 2-ethylhexanoic acid mono 3,5,5-trimethylhexanoic acid monoparamethoxycinnamic acid ester (e), trimethylolpropane mono 2-ethylhexanoic acid diparamethoxycinnamic acid ester (f) and trimethylolpropane mono 3,5,5-trimethylhexanoic acid diparamethoxycinnamic acid (g), wherein the composition ratio (weight ratio) was (a+b):(c+d+e):(f+g)=60.5:34.8:4.7.

Compatibility between sample I and generally used raw materials for cosmetics was excellent, as shown later in Table 2.

Example 8

128.8 g of trimethylolpropane, 136.9 g of paramethoxycinnamic acid and 334.3 g of 3,5,5-trimethylhexanoic acid were used in the esterification and purification treatments in the same manner as in Example 6 to obtain 397 g of a light yellow oily substance (sample J). Sample J had an acid value of 0.1, a hydroxyl value of 0.4, a degree of saponification of 300, a viscosity of 193 centipoise/25° C., and the maximum absorbance was 0.16 at λ max of 312 nm when the ultraviolet light absorption spectrum was measured in the same manner as in Example 1. Gas chromatography analysis indicated that there were 3 types of ingredients, i.e. trimethylolpropane tri 3,5,5-trimethylhexanoic acid ester (a), trimethylolpropane di 3,5,5-trimethylhexanoic acid monoparamethoxycinnamic acid ester (b) and trimethylolpropane mono 3,5,5-trimethylhexanoic acid diparamethoxycinnamic acid ester (c), wherein the composition ratio (weight ratio) was a:b:c=63:32:5. Compatibility between sample J and generally used raw materials for cosmetics was excellent, as shown later in Table 2.

Example 9

110.1 g of trimethylolpropane, 87.7 g of orthomethoxycinnamic acid and 402.2 g of 2-ethylhexanoic acid were used in the esterification and purification treatments in the same manner as in Example 6 to obtain 391 g of a light yellow oily substance (sample K). Sample K had an acid value of 0.1, a hydroxyl value of 0.3, a degree of saponification of 318, a viscosity of 183 centipoise/25° C., and the maximum absorbance was 0.19 at λ max of 312 nm when the ultraviolet light absorption spectrum was measured in the same manner as in Example 6. Gas chromatography analysis indicated that there were 3 types of ingredients, i.e. trimethylolpropane tri 2-ethylhexanoic acid ester (a), trimethylolpropane di 2-ethylhexanoic acid monoorthomethoxycinnamic acid ester (b) and trimethylolpropane mono 2-ethylhexanoic acid diorthomethoxycinnamic acid ester (c), wherein the composition ratio (weight ratio) was a:b:c=62.3:32.8:4.9. Compatibility between sample K and generally used raw materials for cosmetics was excellent, as shown later in Table 2.

Example 10

66.0 g of trimethylolpropane, 43.9 g of paramethoxycinnamic acid and 490.1 g of 2-heptylundecanoic acid were used in the esterification and purification treatments in the same manner as in Example 6 to obtain 389 g of a light yellow oily substance (sample L). Sample L had an acid value of 0.1, a hydroxyl value of 0.3, a degree of saponification of 148, a viscosity of 210 centipoise/25° C., and the maximum absorbance was 0.15 at λ max of 312 nm when the ultraviolet light absorption spectrum was measured in the same manner as in Example 1. Gas chromatography analysis indicated that there were 3 types of ingredients, i.e. trimethylolpropane tri 2-heptylundecanoic acid ester (a), trimethylolpropane di 2-heptylundecanoic acid mono-paramethoxycinnamic acid ester (b) and trimethylolpropane mono 2-heptylundecanoic acid diparamethoxycinnamic acid ester (c), wherein the composition ratio (weight ratio) was a:b:c=63.8:32.2:4.0. Compatibility between sample L and generally (weight ratio) was a:b:c=63.8:32.2:4.0. Compatweight of the sample which dissolves transparently]/[Weight of the material for cosmetics]×100 was calculated and for the values less than 5, between 5 and 80 and 80 or more, the compatibility indicator symbols "X", "Δ" and "○", respectively, were given.

Sample F: (Diparamethoxycinnamic acid glyceryl mono-2-ethylhexanoate: a conventional ultraviolet light absorbent)

Sample G: (Butylmethoxybenzoylmethane: a conventional ultraviolet light absorbent)

TABLE 2

| Raw Materials For Cosmetics | Compatibility | | | | | | |
|---|---|---|---|---|---|---|---|
| | Example H | Example I | Example J | Example K | Example L | Example M | Example N |
| Liquid Paraffin | ○ | ○ | ○ | ○ | Δ | X | X |
| Dimethylpolysiloxane | ○ | ○ | ○ | ○ | Δ | X | X |
| Squalene | ○ | ○ | ○ | ○ | Δ | X | X |
| Isopropyl Myristate | ○ | ○ | ○ | ○ | Δ | X | X |
| Castor Oil | ○ | ○ | ○ | ○ | Δ | X | X | ibility between sample L and generally used raw materials for cosmetics was excellent, as shown later in Table 2.

Comparative Example 1

100.2 g of pentaerythritol and 393.6 g of paramethoxycinnamic acid and 106.2 g of 2-ethylhexanoic acid were used in the esterification and purification treatments in the same manner as in Example 1, followed by the silica-gel column fractionation, to obtain 358 g of a yellow oily substance (pentaerythritol mono 2-ethylhexanoic acid tri-paramethoxycinnamic acid ester). However, this substance had a high viscosity and almost no flowability at 25° C.

Comparative Example 2

96.2 g of pentaerythritol and 503.8 g of paramethoxycinnamic acid were used in the esterification and purification treatments in the same manner as in Example 1, followed by the silica-gel column fractionation, to obtain 385 g of a yellow oily substance (pentaerythritol tetra paramethoxycinnamic acid ester). However, this substance had a high viscosity and almost no flowability at 25° C.

Comparative Example 3

120.4 g of trimethylolpropane and 479.6 g of paramethoxycinnamic acid were used in the esterification and purification treatments in the same manner as in Example 6, followed by the silica-gel column fractionation, to obtain 375 g of a yellow oily substance (trimethylolpropane tetra paramethoxycinnamic acid ester). However, this substance had a high viscosity and almost no flowability at 25° C.

(Note) Method of compatibility testing: The sample was dripped onto 100 g of the material for cosmetics and mixed with it. The maximum weight of the sample which dissolves transparently was determined at 25° C. [The maximum weight of the sample which dissolves transparently]/[Weight of the material for cosmetics]×100 was calculated and for the values less than 5, between 5 and 80 and 80 or more, the compatibility indicator symbols "X", "Δ" and "○", respectively, were given.

Sample M: (Diparamethoxycinnamic acid glyceryl mono-2-ethylhexanoate: a conventional ultraviolet light absorbent)
Sample N: (Butylmethoxybenzoylmethane: a conventional ultraviolet light absorbent)

The ultraviolet light absorbent of the present invention is an oily substance which has a moderate viscosity and therefore can be handled and worked without inconvenience and/or difficulty, and it is an excellent ultraviolet light absorbent with a prescribed ultraviolet light absorbing power.

When the ultraviolet light absorbent of the present invention is used in cosmetics, since it has excellent compatibility with generally used raw materials for cosmetics, the cosmetic containing the ultraviolet light absorbent of the present invention has excellent storage stability and is capable of shielding ultraviolet light and maintaining quality

TABLE 1

| Raw Materials For Cosmetics | Compatibility | | | | | | |
|---|---|---|---|---|---|---|---|
| | Example A | Example B | Example C | Example D | Example E | Example F | Example G |
| Liquid Paraffin | ○ | ○ | ○ | ○ | Δ | X | X |
| Dimethylpolysiloxane | ○ | ○ | ○ | ○ | Δ | X | X |
| Squalene | ○ | ○ | ○ | ○ | Δ | X | X |
| Isopropyl Myristate | ○ | ○ | ○ | ○ | Δ | X | X |
| Castor Oil | ○ | ○ | ○ | ○ | Δ | X | X |

Note) Method of Compatibility testing: The sample was dripped onto 100 g of the material for cosmetics and mixed with it. The maximum weight of the sample which dissolves transparently was determined at 25° C. [The maximum for a long duration of time without causing demulsification, crystal deposition, precipitation, deterioration, etc.

What is claimed is:

1. An ultraviolet light absorbent comprising either mixtures of esters represented by the following formulas (I), (II) and (III), or mixtures of esters represented by the following formulas (IV), (V) and (VI):

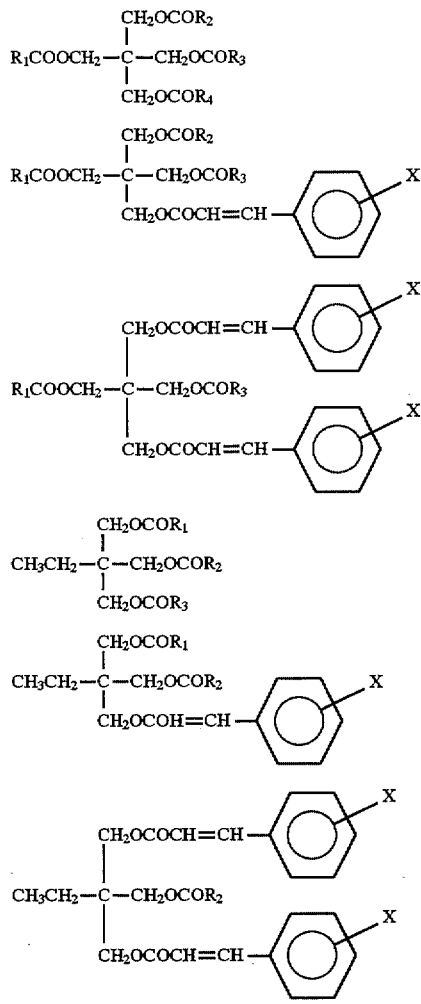

wherein $R_1$, $R_2$, $R_3$ and $R_4$ which can be identical to or different from each other, denote saturated branched-chain alkyl groups with a carbon number of 7-17, and X denotes a methoxyl group with an ortho and/or para position.

2. The ultraviolet light absorbent of claim 1 wherein the composition ratio (weight ratio) of the esters represented by the formulas (I), (II), (III), (IV), (V) and (VI) is (I):(II):(III) :=58–65:30–35:3–7, or (IV):(V):(VI)=58–65:30–35:3–7 and the maximum absorbance of 0.1–0.5 occurs at a peak absorption wavelength of 312 nm when the ultraviolet light absorption spectrum is measured using a 10 ppm ethanol solution.

3. The ultraviolet light absorbent of claim 1 wherein $R_1$, $R_2$, $R_3$ and $R_4$ are all identical and are 2-ethylpentyl, and X denotes a methoxyl group with a para position.

4. The ultraviolet light absorbent of claim 2 wherein $R_1$, $R_2$, $R_3$ and $R_4$ are all identical and are 2-ethylpentyl, and X denotes a methoxyl group with a para position.

5. An ultraviolet light absorbent comprising a mixture of ester compounds obtained by esterification using 3.0–3.8 moles of 2-ethylhexanoic acid and 0.2–1.0 moles of paramethoxycinnamic acid for 1 mole of pentaerythritol.

6. An ultraviolet light absorbent comprising a mixture of ester compounds obtained by esterification using 2.0–2.8 moles of 2-ethylhexanoic acid and 0.2–1.0 moles of paramethoxycinnamic acid for 1 mole of trimethylolpropane.

* * * * *